United States Patent [19]
Gennari

[11] Patent Number: 5,223,500
[45] Date of Patent: * Jun. 29, 1993

[54] STABLE PHARMACEUTICAL COMPOSITION OF ALKALINE OR ALKALINE EARTH 5-METHYL TETRAHYDROFOLATE

[75] Inventor: Federico Gennari, Truccazzano, Italy

[73] Assignee: Bioresearch S.p.A., Milan, Italy

[*] Notice: The portion of the term of this patent subsequent to Jun. 23, 2009 has been disclaimed.

[21] Appl. No.: 814,571

[22] Filed: Dec. 30, 1991

Related U.S. Application Data

[62] Division of Ser. No. 880,098, Jul. 10, 1978, Pat. No. 5,124,452.

[30] Foreign Application Priority Data

Feb. 22, 1977 [GB] United Kingdom .......... 07290/1977

[51] Int. Cl.$^5$ ......................................... A61K 31/505
[52] U.S. Cl. ................................................ 514/249
[58] Field of Search ......................... 514/249; 544/258

[56] References Cited

U.S. PATENT DOCUMENTS

| | | | |
|---|---|---|---|
| 2,695,860 | 11/1954 | Weidenheimer et al. | 514/249 |
| 2,927,113 | 1/1960 | D'Amato | 544/258 |
| 3,870,719 | 3/1975 | Knott et al. | 544/258 |
| 4,148,999 | 4/1979 | Temple, Jr. et al. | 544/258 |
| 4,931,442 | 6/1990 | Blum | 514/249 |
| 4,959,472 | 9/1990 | Wood et al. | 544/258 |
| 5,173,488 | 12/1992 | Haeuer | 514/249 |

FOREIGN PATENT DOCUMENTS

| | | | |
|---|---|---|---|
| 58-38285 | 8/1983 | Japan | 544/258 |
| 649550 | 5/1985 | Switzerland . | |
| 1572138 | 7/1980 | United Kingdom . | |

OTHER PUBLICATIONS

J. A. Blair and Saunders, "A Convenient Method for the Preparation of d,1-5-Methyltetrahydrofolic Acid (d,1-5-methyl-5,6,7,8,-tetrahydropteroly-L-monoglutamic acid)", *Analytical Biochemistry*, 34, 376-381 (1970).

Sakami, "Sodium 5-Methyltetrahydrofolate", *Biochemical Preparations*, No. 10 1963 pp. 103-106.

Gennari, Chem. Abstr. vol. 95 entry 98320p abstracting GB 1572138 (1980).

Primary Examiner—Donald G. Daus
Attorney, Agent, or Firm—Stevens, Davis, Miller & Mosher

[57] ABSTRACT

A method for preparing d,1-5-methyltetrahydrofolic acid and the salts thereof of the formula:

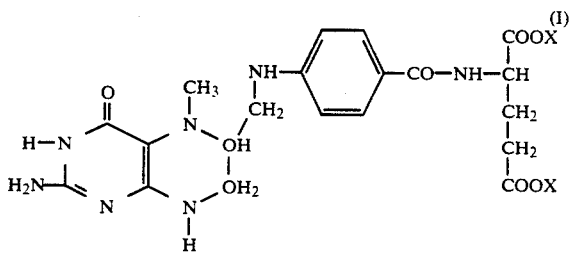

wherein X is hydrogen, an alkaline metal or alkaline earth metal; by reduction of folic acid with sodium borohydride followed by the methylation of the tetrahydrofolic acid thus obtained with aqueous solutions of formaldehye and sodium borohydride in an inert atmosphere.

1 Claim, No Drawings

STABLE PHARMACEUTICAL COMPOSITION OF ALKALINE OR ALKALINE EARTH 5-METHYL TETRAHYDROFOLATE

This is a division of application Ser. No. 880,098, filed Jul. 10, 1978, now U.S. Pat. No. 5,124,452, issued Jun. 23, 1992.

This invention relates to an improved method for preparing d,1-N-[p-(2-amino-3,4,5,6,7,8-hexahydro-5-methyl-4-oxo-6-pteridinyl)methyl]benzoyl glutamic acid and salts of the formula:

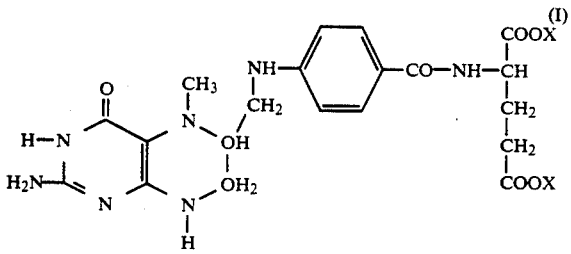

wherein X is hydrogen, an alkaline metal or an alkaline earth metal.

Hereinafter, the acid (I) will be referred to as 5-methyltetrahydrofolic acid (MTHF).

The new process is applicable industrially for obtaining a high purity product simply, economically and with high yields.

BACKGROUND

Notably, d,1-5-methyltetrahydrofolic acid is commonly prepared from folic acid by a process comprising the following essential Steps:

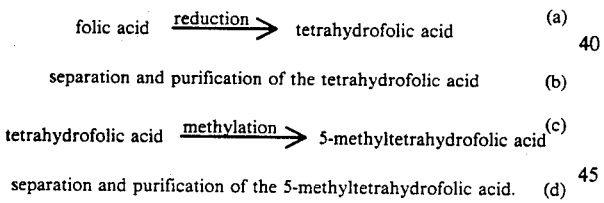

The Step (a) has been carried out both by catalytic hydrogenation and by chemical reduction, in particular by using alkaline borohydrides. (Y. Hetefi et al. - Biochem. Prep. 7, 89 (1960); K. G. Serimgeour et al. - Biochemistry 5, 1438 (1966)). In this Step, no matter what known method is used, a mixture of folic acid, tetrahydrofolic acid and dihydrofolic acid is obtained, consisting mainly of the first two components and difficult to resolve. The only useful methods comprise carrying out Step (b) with very large chromatography columns and using a series of eluents (L. Jaenicke et al. - Z.physio-. Chem. 326, 168 (1961); J. C. Keresztesy et al. - Biochem. Biophysic Res. Commun. 5, 286 (1961); H. Rudiger et al. FE/BS/Letters 4, 316 (1969)). The excess of borohydride in the solution subjected to chromatographic separation is first destroyed by an acid, preferably hydrochloric acid or acetic acid.

The methylation of the tetrahydrofolic acid (Step c) may also be carried out by various methods, the most common and convenient of which comprises reaction with formaldehyde and then reduction with a chemical reducing agent, preferably again an alkaline borohydride (W. Sakami et al., Biochem. Prep. 10, 103 (1963)).

The separation and final purification of the 5-methyltetrahydrofolic acid (Step d) has always been carried out up to the present time by chromatography processes of a greater or lesser complexity, as determined by the nature of the mixture to be purified.

In one modification of said method (J. A. Blair et al., Analytical Biochemistry 34, 376-381 (1970)), Step (b) is dispensed with and the reaction mixture in which the excess borohydride has been destroyed is treated directly with formaldehyde and another alkaline borohydride. Evidently such a modification does not substantially improve the process, because as Step (a) in any case leads to the production of a mixture as heretofore specified, dispensing with Step (b) gives a final mixture which is even more complex and difficult to resolve, with consequent aggravation of the purification Step (d), and a loss in this Step of about 60% of the product.

Furthermore, a high purity product is not obtained as would be required for use in the pharmaceutical field.

In conclusion, said process, which is the best known at the present time, has never gone beyond laboratory use and the production of small quantities of substance for experimental use.

THE INVENTION

It has now been surprisingly found, and it is an object of the present invention, to transform folic acid (a product easily obtainable commercially at economically convenient prices) into d,1-5-methyltetrahydrofolic acid with very high yields and in pharmaceutical purity without the use of costly and complicated Steps of chromatographic purification, if the folic acid is reduced under critical reaction conditions which make it practically 100% selective in producing tetrahydrofolic acid.

The process according to the present invention comprises essentially the following Steps:

(1) Reduction of folic acid to tetrahydrofolic acid by sodium borohydride in an aqueous alkaline solution and an inert gas atmosphere, at a temperature between 60° and 80° C. The ratio of $NaBH_4$ to folic acid lies between 0.5:1 and 3:1, and the reaction time between 30 minutes and 2 hours. On this basis, the preferred reaction conditions are as follows:
ratio of $NaBH_4$ to folic acid 0.7:1, 2:1;
reaction time 1 hour;
pH 7–8; and
temperature 70° C.

(2) Methylation of the tetrahydrofolic acid to 5-methyltetrahydrofolic acid by treatment with a 37% aqueous solution of formaldehyde and then again with sodium borohydride. At the end of the reaction 37% formaldehyde is again added. In this Step the critical reaction conditions are as follows:
pH 6 to 8;
temperature 25°–30° C.;
ratio of 37% formaldehyde:tetrahydrofolic acid between 0.8:1 and 2.5:1;
ratio of $NaBH_4$:tetrahydrofolic acid between 0.25:1–1.5:1;
inert gas atmosphere;
presence of a reducing agent in the final reaction Step (cysteine, reduced glutathione, pantetheine).

On the above basis, the preferred reaction conditions are as follows:

ph 6.5;
temperature 30° C.;
ratio of 37% formaldehyde:tetrahydrofolic acid 1.4:1;
ratio of NaBH$_4$:tetrahydrofolic acid included between 0.5:1 and 1:1;
reducing agent present in the preaction mixture: cysteine.

(3) Separation and purification of the sodium 5-methyltetrahydrofolate. This Step may be performed following two equally advantageous alternatives as a result of the fact that the solution to be treated, according to Step (2) contains essentially only sodium 5-methyltetrahydrofolate:

(A): Separation by adsorption/desorption on active carbon. To carry out this Step, a quantity of active carbon equal to 5-20 times the weight of the initially treated folic acid is made into a pulp in water and added to the final reaction mixture at pH 6.5-6.8 under agitation. The filtered carbon is suspended in an eluent mixture consisting of an alcohol (containing 1 to 4 carbon atoms) or 2 methoxy-ethanol and water in a ratio between 50/50 and 95/5. The eluent mixture also contains a small percentage (0.2 to 1.5%) of a reducing agent, and a small percentage (0.5 to 5%) of ammonia in aqueous solution. The sodium 5-methyltetrahydrofolate may be recovered from the effluent mixture, filtered from the carbon by precipitation with an organic solvent miscible with water, or by concentrating the solution and lyophilising, or again in the form of an alkaline earth salt, from which the 5-methyltetrahydrofolic acid may be released. On the above basis the preferred conditions for the separation and purification Step according to alternative (A) are as follows:

ratio of active carbon: folic acid 7:1;
eluent mixture consisting of ethanol, methanol or 2 methoxyethanol and water in a ratio of 80/20, v/v;
reducing agent in the reaction mixture: cysteine to the extent of 1% of the total eluent mixture; and
34% aqueous ammonia solution to the extent of 2% of the total eluent mixture (0.7% of ammonia).

(B): Separation by direct precipitation of the 5-methyltetrahydrofolic acid from solution as an alkaline-earth metal salt, in particular as a calcium salt. This alternative, still more simple than alternative (A), is particularly useful when Steps (1) and (2) have been carried out in a concentrated aqueous medium and the 5-methyltetrahydrofolic acid has to be separated from a concentrated aqueous solution. The solution resulting from Step (2) is treated with a concentrated aqueous solution of CaCl$_2$ and allowed to remain over about 12 hours at a temperature between about 0° and 5° C. in the presence of a small amount of a reducing agent. The thus precipitated calcium methyl-tetrahydrofolate pentahydrate is purified by dissolution in a small volume of boiling water and recrystallized by leaving the solution at 0°-5° C. The preferred ratio of folic acid to CaCl$_2$ is between about 2:1 and 3:1 and, preferably, 2.5:1. The reducing product is preferably selected in the group consisting of cysteine, cysteamine, reduced glutathione, pantetheine.

The product obtained by the present process has a purity exceeding 99% and it is obtained in yields always exceeding 80% with respect to the initial folic acid.

The Steps heretofore described are carried out in succession in the same reactor, without separating intermediate products.

The ratios indicated are always ratios by weight.

Comparing the new process according to the invention with the best process of the known art, the essential Steps of which are summarized hereinbefore, it is immediately apparent that the present process makes it possible to dispense with both the intermediate Step and final Step of chromatographic separation and purification.

This not only leads to considerable simplification and economy, with known processes requiring long and costly columns and long processing times, but it also affords a considerable increase in yield because know chromatographic separations result in large losses of useful product.

Further losses arise in recovering the product from very dilute solutions. Such recovery is also obviously very costly.

The final separation and purification stage is replaced by the adsorption/desorption Step on active carbon or by the precipitation with Ca salts which are extremely simple and which afford high yield. These Steps are completely new in the production of 5-methyltetrahydrofolic acid and its salts.

From the description given heretofore, it can be seen that the entire production process for 5-methyltetrahydrofolic acid is conducted in the presence of inert gas, and in some Steps in the presence of a reducing agent. This is due to the need to prevent self-oxidation either of the tetrahydrofolic acid or of the 5-methyltetrahydrofolic acid to the corresponding dihydrofolic and folic acids.

The same self-oxidation problem occurs in preserving the 5-methyltetrahydrofolic acid.

Up to the present time, the reducing agents suggested for conserving MTHF acid were 2-mercaptoethanol and ascorbic acid. Obviously these substances meant that no industrial use of the product in the pharmaceutical field could be considered and, accordingly, they were limited to laboratory use.

Thus, 2-mercaptoethanol is a toxic product of nauseating odor, while ascorbic acid decomposes rapidly at the optimum pH values of 7-8 for injectable solutions.

A further object of the present invention is to provide stabilised compositions of alkaline or alkaline earth 5-methyltetrahydrofolates for pharmaceutical use.

The new stable compositions consist essentially of 5-methyltetrahydrofolate (as active substance) and 5 to 50% of an organic compound of biological origin containing at least one —SH group (as stabliser). Characteristic compounds of this class are for example cysteine, cysteamine, pantetheine, reduced glutathione and all such derivatives in which the —SH function is maintained active.

All of these substances are without toxicity, are stable at physiological pH values and are therefore suitable for the preparation of liquid or solid pharmaceutical compounds for any type of application in the human field.

The new pharmaceutical compositions possess hemopoietic action, protective activity on the liver and antineoplastic activity. Some practical examples of the process are given hereinafter in order to better illustrate and facilitate the reproduction of the process according to the present invention.

It is apparent that these examples are not limiting, and the reaction conditions may be varied within the limits defined in the specification and incorporate all the expedients well known or immediately evident to an expert of the art.

EXAMPLE 1

5-Methyltetrahydrofolic Acid and Calcium Salt 80 l of deionised water are fed into a reactor and 2.4 kg of d,l-folic acid are suspended therein. Solid $Na_2CO_3$ is added under agitation until the folic acid is completely dissolved (final solution pH 7.8), then 4.8 kg of $NaBH_4$ dissolved in 40 l of $H_2O$ are added and the reaction mixture heated to 70° C. The mixture is reacted for 1 hour under agitation while constantly under a stream of nitrogen. When the reaction is finished the reactor is cooled to 30° C. and 3.5 kg of 37% aqueous formaldehyde and 2.4 kg of sodium borohydride dissolved in 20 l of water are added under agitation. The reaction is continued for 1 hour under agitation in a stream of nitrogen. After this time, a further 0.15 kg of 37% formaldehyde and 1 kg of cysteine are added.

17 kg of active carbon are suspended in 100 l of deaerated water and the carbon suspension is added under agitation to the reaction mixture brought to pH 6.5. After a few minutes it is filtered under nitrogen and the carbon cake on the filter is washed with water containing 1% of cysteine until all the inorganic salts have been completely removed. The carbon is suspended in 100 l of an eluent mixture of the following volumetric composition:

2-methoxy-ethanol 80, water (containing 5% of cysteine) 20, ammonia (34%) 2.

The suspension is left under agitation for some minutes, is then filtered and the filtrate concentrated to a volume of 20 liters. The concentrated filtrate is poured into a solution containing 700 g of $CaCl_2$ in 100 liters of ethanol.

Calcium 5-methyltetrahydrofolate precipitates and is filtered off under nitrogen, washed with ethanol and then dried under vacuum. 2.3 kg of product are obtained, equal to a yield of 86% on the initial folic acid.

On U.V. analysis the product shows the following characteristics (pH=7; $\epsilon$=32.10$^3$):
  maximum absorption at 290 nm
  minimum absorption at 245 nm
  ratio $E_{290}/E_{245}$=3.8.

Analysis over a Sephadex DEAE A-25 chromatographic column using the method of Nixon and Bertino (P. F. Nixon, J. R. Bertino, Methods in Enzym. 18, 661 (1971)) shows only the 5-methyltetrahydrofolic acid peak. HPLC anaylysis (Partisil-10SAX 4.6×250 mm column; eluent 5% ammonium citrate; pH=6) shows only the 5-methyltetrahydrofolic acid peak. NMR spectrum: singlet characteristic of the $N_5$—$CH_3$ group at $\tau$=7.5. 1 kg of the calcium 5-methyltetrahydrofolate prepared in this manner is dissolved in 40 l of water containing 1 kg of cysteine under heat and nitrogen.

The pH is brought to 6 with dilute hydrochloric acid and the mixture allowed to stand in a refrigerator.

5-methyltetrahydrofolic acid precipitates and is filtered off, washed with a little cold water and dried. The product shows an $E_{290}/E_{245}$ value of 3.8.

The same process was repeated but replacing the 2-methoxy-ethanol in the eluent mixture with ethanol, methanol, 1 or 2-propanol, n-butanol, t-butanol, sec-butanol and isobutanol respectively. In each case a product was obtained of the same characteristics and the same yield.

EXAMPLE 2

Calcium 5-Methyltetrahydrofolate

5-Methyltetrahydrofolic acid is prepared as described in Example 1. The carbon is eluted with a mixture of the following composition:

methanol 80, water (containing 5% of reduced glutathione) 20, ammonia (34%) 2.

After filtering the active carbon, 700 g of $CaCl_2$ dissolved in a little water are added to the eluate.

Calcium 5-methyltetrahydrofolate precipitates and is filtered off under a stream of nitrogen, washed with ethanol and dried under vacuum.

2.1 kg of product are obtained, equal to a yield of 80% of folic acid.

The product has the same characteristics as that obtained in Example 1.

EXAMPLE 3

Sodium 5-Methyltetrahydrofolate

The procedure of Example 1 is followed including the treatment of the carbon cake with the eluent mixture consisting of 2-propanol and water containing small percentages of ammonium hydrate and cysteine, the filtered eluate then being concentrated to a volume of 20 liters.

The solution is subjected to lyophylisation to afford 2.1 kg of sodium 5-methyltetrahydrofolate in a yield of 80%.

The product shows a $E_{290}/E_{245}$ value of 3.8.

EXAMPLE 4

Barium 5-Methyltetrahydrofolate

The procedure of Example 1 is followed including the concentration of the eluate. In this test the eluate is treated with 1.3 kg of $BaCl_2$ dissolved in 100 liters of ethanol.

Barium 5-methyltetrahydrofolate precipitates in a yield of 83%. $E_{290}/E_{245}$=3.79.

EXAMPLE 5

Magnesium 5-Methyltetrahydrofolate

The procedure of Example 1 is followed including the concentration of the eluate. In this test the eluate is treated with 0.6 kg of $MgCl_2$ dissolved in 100 liters of ethanol.

Magnesium 5-methyltetrahydrofolate precipitates in a yield of 82%. $E_{290}/E_{245}$=3.8.

EXAMPLE 6

Sodium 5-Methyltetrahydrofolate 100 grams of calcium 5-methyltetrahydrofolate, prepared as described under Example 1, are dissolved in 4 liters of $H_2O$.

A stoichiometric quantity of $Na_2SO_4$ is added to this solution.

$CaSO_4$ is precipitated and separated by filtration.

The clear solution is subjected to lyophilisation, to afford sodium 5-methyltetrahydrofolate.

EXAMPLE 7

Calcium 5-Methyltetrahydrofolate and Pentahydrate 2.50 kg of folic acid are suspended into 10 l of water and 1 l of 40% $Na_2CO_3$ is added under stirring.

The pH is adjusted to 7.8 with $Na_2CO_3$ and, after cooling, 1.700 kg of $NaBH_4$ are added under nitrogen atmosphere.

The mixture is left to react over 2 hours while heating at about 70° C. to complete the reaction; 4.00 kg of 37% aqueous formaldehyde are added and thereafter 0.80 kg of sodium borohydride.

The precipitated sodium borate is filtered and the excess borohydride is destroyed by adjusting the pH of the solution to 6 with HCl. 1 kg of $CaCl_2$ dissolved into 2 l of water are added while stirring and the obtained reaction mixture is left at 3° C. overnight.

The calcium methyltetrahydrofolate precipitates as an amorphous white powder which is filtered and washed with water.

This salt is dissolved into 10 l of boiling water and the cooled solution is left to rest overnight.

The precipitated crystalline salt is filtered, washing and dried under vacuum.

2.40 kg of calcium 5-methyltetrahydrofolate pentahydrate are obtained with an overall yield of 80% over the starting folic acid.

Under identical conditions the Mg salt is also obtained, which however, it is somewhat difficult to filtrate.

As stated, 5-methyltetrahydrofolic acid and its salts, as obtained by the present process, may be used as an active ingredient to afford stable therapeutic compositions at ambient temperature if mixed with 5 to 50% of a stabilising substance chosen from the group consisting of compounds of biological origin containing at least one mercapto (—SH) group.

Typical of the compounds of this class are cysteine, cysteamine, pantetheine and reduced glutathione.

To illustrate this aspect of the invention, a typical formulation using the aforesaid compound as the active ingredient is given hereinafter.

EXAMPLE 8

Oral and Injectable Formulations

| Oral Formulation: | |
| --- | --- |
| Tablets | |
| Active Compound | 25 mg |
| Stabiliser | 12.5 mg |
| Excipients for compression, quantity necessary to make up 150 mg. | |
| Injectable Formulation: | |
| Active Compound | 25 mg/ml |
| Stabiliser | 12.5 mg/ml |
| Lyophilisation | 150 mg/ml |

When necessary, the solution is brought to pH 7.5 with concentrated NaOH, fed into a phial and lyophilised.

In this Example the term "Active Compound" means:
5-methyltetrahydrofolic acid
sodium 5-methyltetrahydrofolate
calcium 5-methyltetrahydrofolate
magnesium 5-methyltetrahydrofolate In this Examples the term "stabiliser" means:
cysteine
cysteamine
pantetheine
reduced glutathione The term "lyophilisation support" signifies any substance which may fall within this definition in usual lyophilisation technology, such as glycine.

In no instance did the resulting solution show any alteration of the product during its retention in the phial or during lyophilisation.

What is claimed is:

1. A stable therapeutic composition consisting essentially of an alkali or calcium or magnesium salt of 5-methyl tetrahydrofolic acid and 5-50% of an organic compound of biological origin containing at least one —SH group and selected from the group consisting of cysteine, cysteamine, pantetheine and reduced glutathione.

* * * * *